(12) United States Patent
Fujita et al.

(10) Patent No.: US 12,138,897 B2
(45) Date of Patent: Nov. 12, 2024

(54) DEVICE AND METHOD FOR MANUFACTURING LAYERED SHEET

(71) Applicant: ZUIKO CORPORATION, Ibaraki (JP)

(72) Inventors: Yukihiko Fujita, Ibaraki (JP); Hideyuki Nakamura, Ibaraki (JP)

(73) Assignee: ZUIKO CORPORATION, Ibaraki (JP)

(*) Notice: Subject to any disclaimer, the term of this patent is extended or adjusted under 35 U.S.C. 154(b) by 80 days.

(21) Appl. No.: 17/796,473

(22) PCT Filed: Feb. 9, 2021

(86) PCT No.: PCT/JP2021/004721
§ 371 (c)(1),
(2) Date: Jul. 29, 2022

(87) PCT Pub. No.: WO2021/161979
PCT Pub. Date: Aug. 19, 2021

(65) Prior Publication Data
US 2023/0294391 A1 Sep. 21, 2023

(30) Foreign Application Priority Data
Feb. 13, 2020 (JP) ................................ 2020-022889

(51) Int. Cl.
*B32B 41/00* (2006.01)
*B32B 37/00* (2006.01)
*B32B 37/10* (2006.01)

(52) U.S. Cl.
CPC .......... *B32B 41/00* (2013.01); *B32B 37/0053* (2013.01); *B32B 37/10* (2013.01)

(58) Field of Classification Search
CPC ..... B32B 41/00; B32B 37/0053; B32B 37/10; B29C 65/7894; B29C 66/0062;
(Continued)

(56) References Cited

U.S. PATENT DOCUMENTS

| 5,174,562 A | 12/1992 | Mizunaga et al. |
| 2002/0053766 A1 | 5/2002 | Kubota |

(Continued)

FOREIGN PATENT DOCUMENTS

| CN | 1717313 A | 1/2006 |
| CN | 204679054 U | 9/2015 |

(Continued)

OTHER PUBLICATIONS

PCT/ISA/210, "International Search Report for PCT International Application No. PCT/JP2021/004721," Apr. 26, 2021.
(Continued)

*Primary Examiner* — Michael N Orlando
*Assistant Examiner* — Joshel Rivera
(74) *Attorney, Agent, or Firm* — HAUPTMAN HAM, LLP (57) ABSTRACT

A layered body containing continuous sheets is thermally fused when passing through a space between an anvil roll and an energy applying device to form a layered sheet. A nip stage for sandwiching the layered body is provided upstream of the space between the anvil roll and the energy applying device. The nip stage includes at least one displacement member which is displaced in accordance with the thickness of the layered body sandwiched by the nip stage. Whether the thickness of the layered body sandwiched by the nip stage has deviated from a reference range is detected on the basis of the displacement of the displacement member, and when it is detected that the thickness has deviated from the reference range, the energy applying device is caused to retreat in a direction going away from the anvil roll.

12 Claims, 7 Drawing Sheets

(58) Field of Classification Search
CPC . B29C 66/1122; B29C 66/344; B29C 66/433; B29C 66/7373; B29C 66/73921; B29C 66/8145; B29C 66/8242; B29C 66/83411; B29C 66/83415; B29C 66/874; B29C 66/87443; B29C 66/954; B29C 66/7294; B29C 65/086; A61F 13/15593; B29K 2995/0046; B29L 2031/4878
USPC .................. 156/60, 64, 350, 351, 378, 379
See application file for complete search history.

(56) References Cited

U.S. PATENT DOCUMENTS

| | | | |
|---|---|---|---|
| 2005/0145317 | A1 | 7/2005 | Yamamoto |
| 2016/0100990 | A1 | 4/2016 | Fujita et al. |
| 2017/0050423 | A1 | 2/2017 | Yamamoto et al. |
| 2018/0363182 | A1 | 12/2018 | Bergmann et al. |
| 2020/0361158 | A1* | 11/2020 | Sugiura .................. B29C 66/43 |
| 2021/0031428 | A1 | 2/2021 | Nakamura et al. |

FOREIGN PATENT DOCUMENTS

| | | | | |
|---|---|---|---|---|
| CN | 105377532 | A | | 3/2016 |
| CN | 108368655 | A | | 8/2018 |
| EP | 1609582 | B1 | * | 2/2008 ....... A61F 13/15739 |
| JP | S63-256808 | A | | 10/1988 |
| JP | H02-15944 | U | | 2/1990 |
| JP | 2016-182214 | A | | 10/2016 |
| JP | 2016-112340 | A | | 11/2016 |
| SU | 1519915 | A1 | | 11/1989 |
| WO | WO-2019054314 | A1 | * | 3/2019 ....... A61F 13/15723 |
| WO | 2019/155765 | A1 | | 8/2019 |

OTHER PUBLICATIONS

European Patent Office, "Extended European Search Report with Search Opinion for European Patent Application No. 21753652.3," Jun. 7, 2023.

China National Intellectual Property Administration, "Office Action for Chinese Patent Application No. 202180013504.5," Jan. 16, 2024.

China National Intellectual Property Administration, "Search Report for Chinese Patent Application No. 202180013504.5," Jan. 12, 2024.

* cited by examiner

DEVICE AND METHOD FOR MANUFACTURING LAYERED SHEET

RELATED APPLICATIONS

The present application is National Phase of International Application No. PCT/JP2021/004721 filed Feb. 9, 2021, and claim priority from Japanese Application No. 2020-022889, filed Feb. 13, 2020, the disclosures of which are hereby incorporated by reference herein in its entirety.

TECHNICAL FIELD

The present invention relates to a device and a method for manufacturing a layered sheet, and more specifically, relates to a technology to continuously manufacture a layered sheet.

BACKGROUND ART

Figure 7:
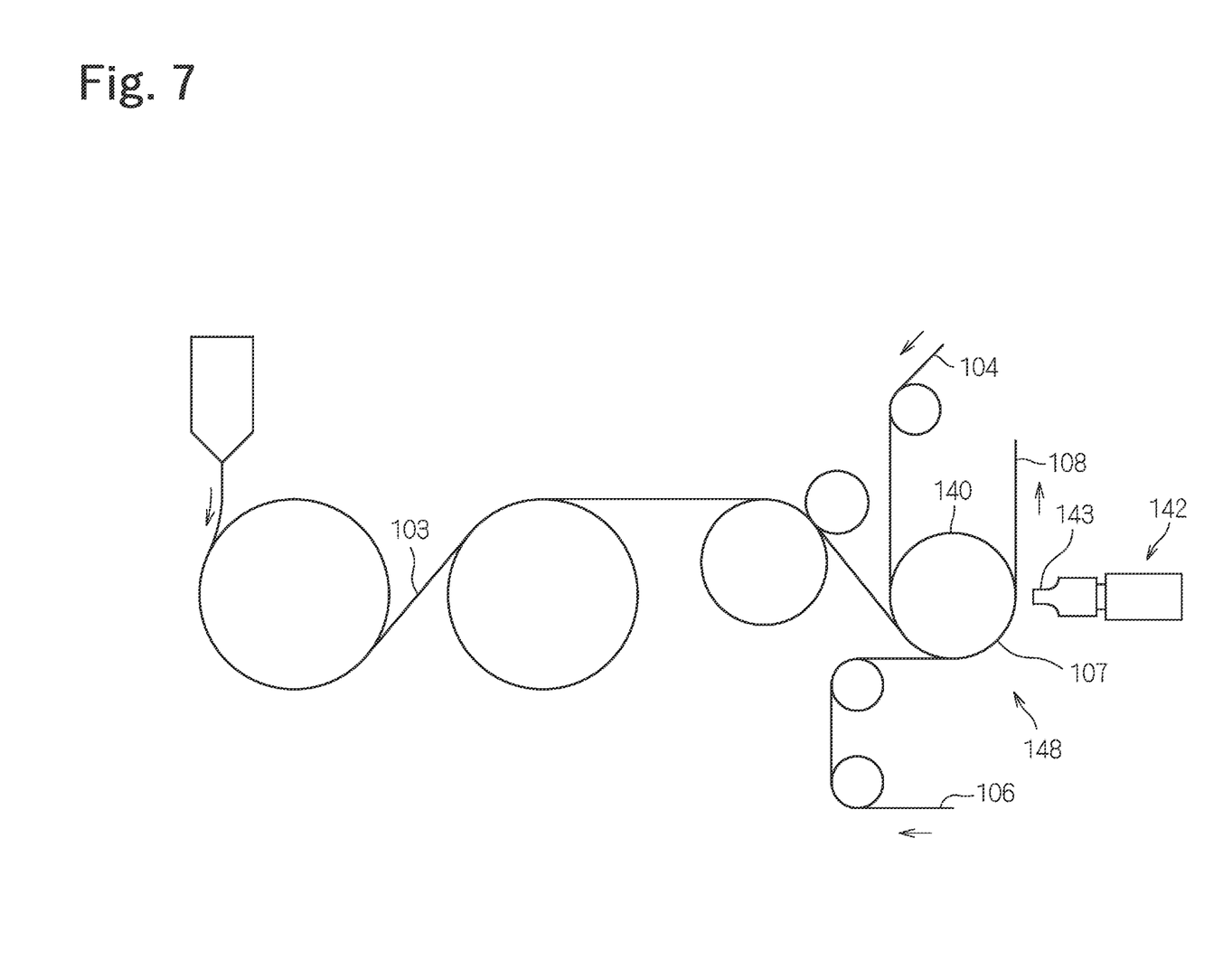
FIG. 7 is a schematic view of the layered sheet manufacturing device (conventional example).

Layered sheets used for disposable diapers and the like are continuously manufactured. For example, in a layered sheet manufacturing device 148 shown in a schematic view of FIG. 7, when a layered body 107 where an elastic stretchable member 103 is laminated between a first and second continuous sheets 104 and 106 passes through a space between an anvil roll 140 and an ultrasonic horn 143 of an energy applying device 142, the layers 103, 104 and 106 of the layered body 107 are thermally fused together to manufacture a layered sheet 108 (for example, see Patent Literature 1).

CITATION LIST

Patent Literature

[Patent Literature 1] WO 2019/155765

SUMMARY OF THE INVENTION

Problem to be Solved by the Invention

In the manufacturing process of continuously forming a layered sheet by integrating a layered body where a plurality of sheets or a sheet and another layer are laminated one on another, by passing it through a space between an anvil roll and an energy applying device so that appropriate parts are thermally fused together as described above, if a part where the thickness of the layered body is changed by a breakage end or a foreign substance is introduced into the space between the anvil roll and the energy applying device as it is when a specific layer is broken upstream of the energy applying device or when a foreign substance is mixed in between layers, a high load is applied to the energy applying device to cause an adverse effect such as breakage.

In view of such circumstances, a problem to be solved by the present invention is to provide a device and a method for manufacturing a layered sheet with which it is possible to prevent adverse effects, caused by a change in the thickness of the layered body, from influencing the energy applying device.

Means for Solving the Problem

To solve the above-mentioned problem, the present invention provides a layered sheet manufacturing device structured as follows:

The layered sheet manufacturing device is provided with: (a) an anvil roll that faces a predetermined path along which a layered body containing at least one continuous sheet is conveyed; (b) an energy applying device disposed so as to face the anvil roll across the predetermined path and applying an energy for thermally fusing layers of the layered body together, to the layered body being conveyed along the predetermined path; (c) a nip stage including a first and second members sandwiching the layered body in a thickness direction upstream of a space between the anvil roll and the energy applying device, at least one of the first and second members being a displacement member displaced according to a thickness of a part of the layered body sandwiched between the first and second members; (d) a detection device that detects whether the thickness has deviated from a predetermined reference range or not on the basis of a displacement of the displacement member; and (e) a retreat device that causes the energy applying device to retreat in a direction going away from the anvil roll when the detection device detects that the thickness has deviated from the reference range.

The above-described structure enables the following: The space between the anvil roll and the energy applying device is increased before the non-reference part of the layered body the thickness of which has deviated from the reference range reaches the space between the anvil roll and the energy applying device, and the energy applying device is away from the non-reference part when the non-reference part reaches the space between the anvil roll and the energy applying device. This makes it possible to prevent adverse effects, caused by a change in the thickness of the layered body, from influencing the energy applying device.

Preferably, the energy applying device comes into contact with the layered body to apply a vibrational energy or a thermal energy to the layered body.

In this case, an effect is great of preventing adverse effects from influencing the energy applying device by causing the energy applying device to retreat in a direction going away from the anvil roll.

Preferably, the nip stage is structured so as to sandwich the layered body in a direction of the thickness between the anvil roll and the displacement member.

In this case, the structure of the nip stage is simple compared with when the nip stage is structured separately from the anvil roll.

Preferably, the detection device includes: (i) a lever that swings according to the displacement of the displacement member and having a predetermined part displaced more largely than the displacement member; and (ii) a sensor that detects a displacement of the predetermined part of the lever.

In this case, the displacement of the displacement member can be amplified by the lever, and by the displacement of the predetermined part where the displacement of the displacement member is amplified, it can be easily detected that the thickness of the layered body has deviated from the reference range.

Preferably, the layered sheet manufacturing device is further provided with (f) a feeding roll that feeds an elastic stretchable member of which the layered body is to be formed, toward the anvil roll. The feeding roll rotates at a peripheral speed lower than a peripheral speed of the anvil roll.

In this case, the layered sheet having stretchability can be manufactured by stretching the elastic stretchable member between the feeding roll and the nip stage and thermally fusing the layers of the layered body under the condition where the elastic stretchable member is stretched.

More preferably, the layered sheet manufacturing device is further provided with (g) a stopper disposed in an intermediate position between the nip stage and the feeding roll and when the elastic stretchable member breaks downstream of the intermediate position, inhibiting a breakage end upstream of a broken part of the elastic stretchable member from returning toward the feeding roll beyond the intermediate position.

In this case, even if the elastic stretchable member breaks, the breakage end (the end portion formed by the breakage) upstream of the elastic stretchable member can be made to remain downstream of the stopper, so that continuous operation is facilitated.

Moreover, to solve the above-mentioned problem, the present invention provides a layered sheet manufacturing method structured as follows:

The layered sheet manufacturing method is provided with: (i) a conveyance process in which a layered body containing at least one continuous sheet is conveyed along a predetermined path; (ii) a thermal fusion process in which an anvil roll and an energy applying device are disposed so as to sandwich the predetermined path and an energy for thermally fusing layers of the layered body together is applied from the energy applying device to a part of the layered body passing through a space between the anvil roll and the energy applying device; (iii) a detection process in which a nip stage is provided where a first and second members are included that sandwich the layered body in a thickness direction upstream of the space between the anvil roll and the energy applying device and at least one of the first and second members is a displacement member displaced in accordance with a thickness of the part of the layered body sandwiched between the first and second members, and whether the thickness has deviated from a predetermined reference range or not is determined on the basis of a displacement of the displacement member; and (iv) a retreat process in which when it is determined that the thickness has deviated from the reference range in the detection process, the energy applying device is caused to retreat in the direction going away from the anvil roll.

The above-described structure enables the following: The space between the anvil roll and the energy applying device is increased before the non-reference part of the layered body the thickness of which has deviated from the reference range reaches the space between the anvil roll and the energy applying device, and the energy applying device is away from the non-reference part when the non-reference part reaches the space between the anvil roll and the energy applying device. This makes it possible to prevent adverse effects, caused by a change in the thickness of the layered body, from influencing the energy applying device.

Preferably, the energy applying device comes into contact with the layered body to apply a vibrational energy or a thermal energy to the layered body.

In this case, an effect is great of preventing adverse effects from influencing the energy applying device by causing the energy applying device to retreat in a direction going away from the anvil roll.

Preferably, the nip stage is structured so as to sandwich the layered body in a direction of the thickness between the anvil roll and the displacement member.

In this case, the structure of the nip stage is simple compared with when the nip stage is structured separately from the anvil roll.

Preferably, in the detection process, by using (a) a lever that swings according to the displacement of the displacement member and having a predetermined part displaced more largely than the displacement member and (b) a sensor that detects a displacement of the predetermined part of the lever, it is detected whether the thickness has deviated from the reference range or not.

In this case, the displacement of the displacement member can be amplified by the lever, and by the displacement of the predetermined part where the displacement of the displacement member is amplified, it can be easily detected that the thickness of the layered body has deviated from the reference range.

Preferably, the layered sheet manufacturing method is further provided with (v) a stretching process in which a feeding roll that feeds an elastic stretchable member of which the layered body is to be formed, toward the anvil roll rotates at a peripheral speed lower than a peripheral speed of the anvil roll.

In this case, the layered sheet having stretchability can be manufactured by stretching the elastic stretchable member between the feeding roll and the nip stage and thermally fusing the layers of the layered body under the condition where the elastic stretchable member is stretched.

Preferably, the layered sheet manufacturing method is further provided with (vi) a return inhibition process in which a stopper is disposed in an intermediate position between the nip stage and the feeding roll and when the elastic stretchable member breaks downstream of the intermediate position, the stopper inhibits a breakage end upstream of a broken part of the elastic stretchable member from returning toward the feeding roll beyond the intermediate position.

In this case, even if the elastic stretchable member breaks, the breakage end (the end portion formed by the breakage) upstream of the elastic stretchable member can be made to remain downstream of the stopper, so that continuous operation is facilitated.

Effects of the Invention

According to the present invention, it is possible to prevent adverse effects, caused by a change in the thickness of the layered body, from influencing the energy applying device.

MODE FOR CARRYING OUT THE INVENTION

Hereinafter, embodiments of the present invention will be described with reference to the drawings.

<First embodiment> A layered sheet manufacturing device 10 and a method for manufacturing a layered sheet 8 according to a first embodiment will be described with reference to FIGS. 1 to 4.

Figure 1:
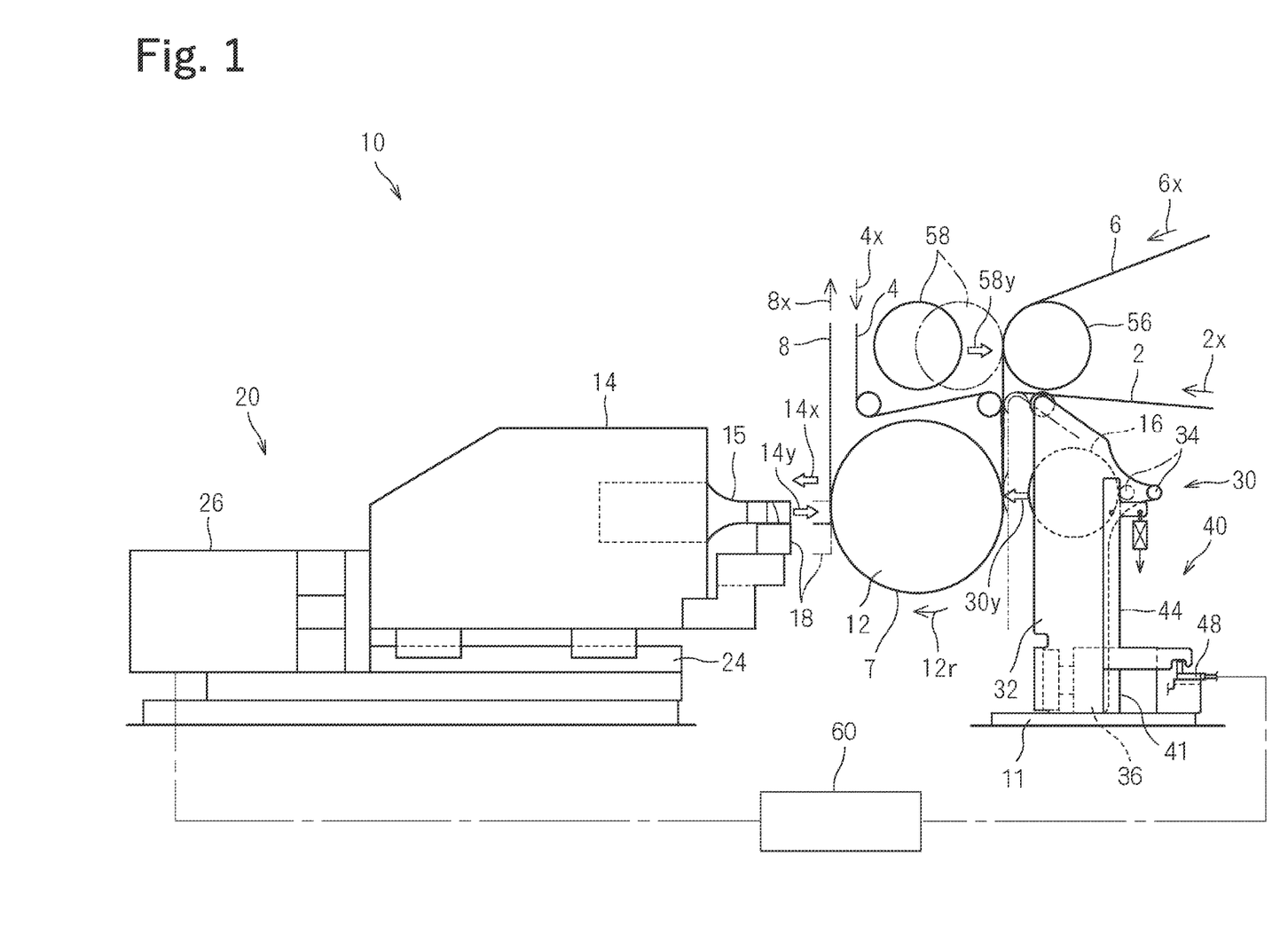
FIG. 1 is a schematic view showing a general structure of a layered sheet manufacturing device (first embodiment).
Figure 2:
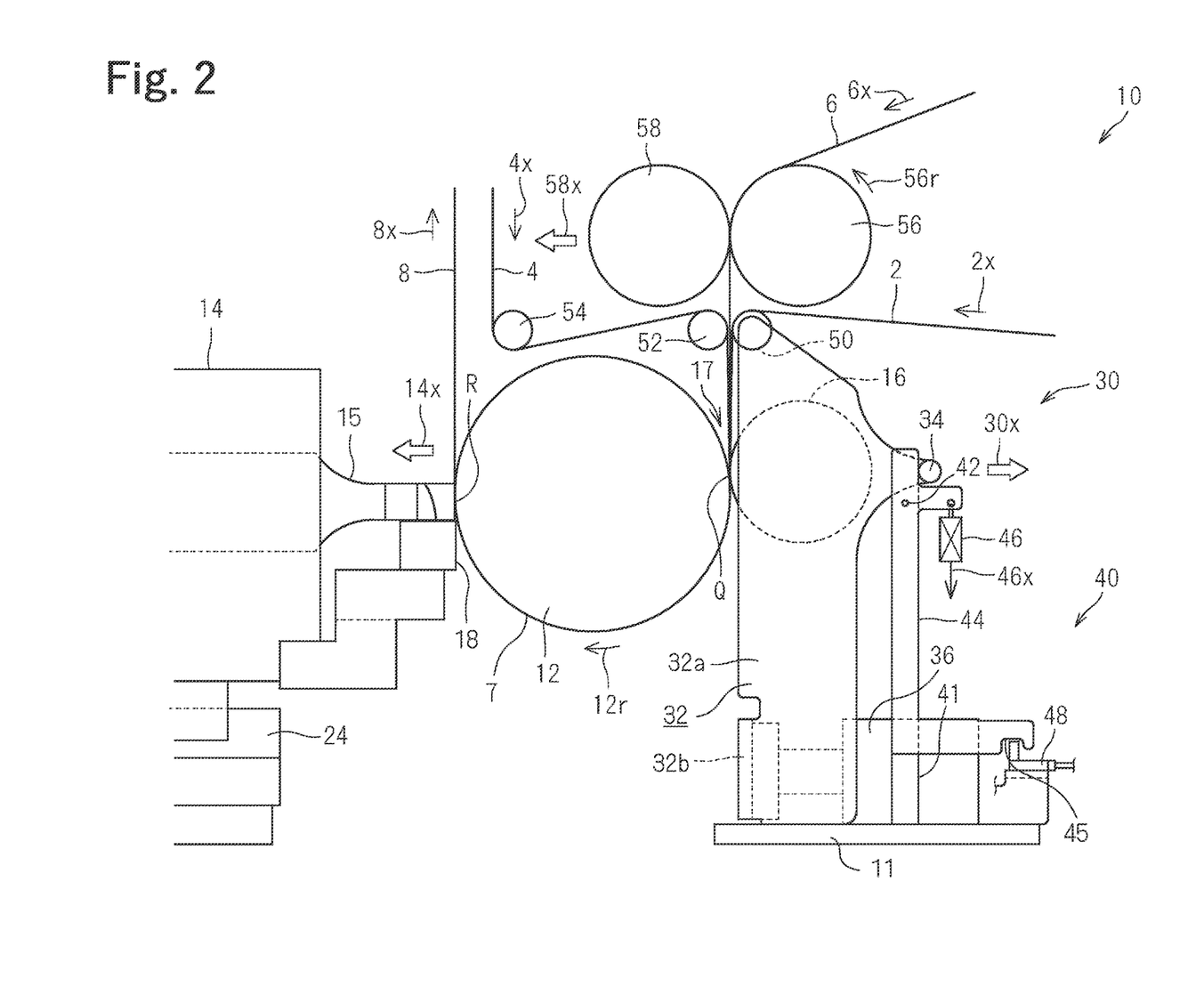
FIG. 2 is a relevant part enlarged view of the layered sheet manufacturing device (first embodiment).

FIG. 1 is a schematic view showing a general structure of the layered sheet manufacturing device 10, and the retreat condition before operation or after operation is shown by the solid line. FIG. 2 is a relevant part enlarged view of the layered sheet manufacturing device 10, and shows the condition during operation.

As shown in FIGS. 1 and 2, the layered sheet manufacturing device 10 is generally provided with an anvil roll 12, an energy applying device 14, a nip roll 16, a retreat device 20, a nip roll support mechanism 30, a detection device 40 and a control device 60.

A first and second continuous sheets 2 and 4 and an elastic stretchable member 6 are conveyed in the directions indicated by the arrows 2x, 4x and 6x, and a layered body 7 where the elastic stretchable member 6 is laminated between the first and second continuous sheets 2 and 4 is conveyed along the outer peripheral surface of the anvil roll 12 rotated in the direction indicated by the arrow 12r. The anvil roll 12 faces a predetermined path along which the layered body 7 is conveyed.

For example, the first and second continuous sheets 2 and 4 are belt-like nonwoven fabric sheets. The elastic stretchable member 6 is a sheet-like, belt-like or cord-like member of an elastic stretchable sheet, a thread rubber or the like, and stretches when applied with a tensile force and returns to its original size when the tensile force is removed.

The first continuous sheet 2 is conveyed from a first stopper roll 50 toward the anvil roll 12. The second continuous sheet 4 is conveyed toward the anvil roll 12 by way of a guide roll 54 and a second stopper roll 52. The elastic stretchable member 6 is fed from a feeding roll 56 rotated in the direction indicated by the arrow 56r, and passes between the first and second stopper rolls 50 and 52 to be conveyed to the anvil roll 12. The elastic stretchable member 6 is fed while being sandwiched between an opposite roll 58 pushed in the direction indicated by the arrow 58y and the feeding roll 56.

The energy applying device 14 is disposed so as to face the anvil roll 12 across the predetermined path along which the layered body 7 is conveyed. The energy applying device 14 is, for example, an ultrasonic sealing device 14 having an ultrasonic horn 15. The ultrasonic horn 15 comes into contact with the part of the layered body 7 passing through the space between the anvil roll 12 and the energy applying device 14, and provides the layered body 7 with a vibrational energy for thermally fusing the layers 2, 4 and 6 of the layered body 7 together. The energy applying device 14 may be a heat sealing device in which a contact part that becomes high in temperature comes into contact with the layered body 7 to provide a thermal energy.

The layers 2, 4 and 6 are integrated by appropriate parts of the layered body 7 being thermally fused, thereby forming the layered sheet 8. The layered sheet 8 is conveyed in the direction indicated by the arrow 8x.

As shown in FIG. 1, the retreat device 20 moves the energy applying device 14 held so as to be movable along a guide mechanism 24, to a retreat position shown in FIG. 1 and to a position during operation shown in FIG. 2 as shown by the arrows 14x and 14y by the extension and contraction of a piston rod of an air cylinder 26.

As shown in FIG. 2, at a position Q upstream of the space R between the anvil roll 12 and the energy applying device 14, a nip stage 17 that sandwiches the layered body 7 in the thickness direction is provided between the anvil roll 12 and the nip roll 16. The nip roll 16 is supported by the nip roll support mechanism 30 so as to be displaced in accordance with the thickness of the part of the layered body 7 sandwiched between the anvil roll 12 and the nip roll 16.

The anvil roll 12 and the nip roll 16 are the first and second members 12 and 16 included by the nip stage 17. The nip roll 16 is the displacement member 16, and is displaced in accordance with the thickness of the part of the layered body 7 sandwiched between the anvil roll 12 and the nip roll 16. The nip roll 16 may be rotatable, or may be rotated in synchronism with the anvil roll 12. The nip stage 17 may be structured so that the entire part of the layered body 7 in the width direction is sandwiched between the anvil roll 12 and the nip roll 16, or may be structured so that a part of the layered body 7 in the width direction is sandwiched between the anvil roll 12 and the nip roll 16 by using a stepped roll as the nip roll 16. Instead of the nip roll 16, a plate-like member or the like that comes into contact with the layered body 7 without rotating may be used.

The nip roll support mechanism 30 is provided with a nip roll support portion 32 displaced integrally with the nip roll 16 and an air cylinder 36 that moves the nip roll support portion 32. In the nip roll support portion 32, a pair of side plates 32a supporting the nip roll 16 rotatably and parallel to the anvil roll 12 are fixed to both ends of a coupling member 32b extending parallel to the anvil roll 12. The air cylinder 36 is connected to the coupling member 32b of the nip roll support portion 32.

The nip roll support portion 32 is moved along a machine base 11 by the extension and contraction of the piston rod of the air cylinder 36 in a direction in which the nip roll 16 is pressed against the anvil roll 12 (the direction indicated by the arrow 30y in FIG. 1) or in a direction in which the nip roll 16 is separated from the anvil roll 12 (the direction indicated by the arrow 30x in FIG. 20).

When the layered sheet 8 is manufactured, the air cylinder 36 presses the nip roll 16 toward the anvil roll 12 through the nip roll support portion 32, and the layered body 7 is sandwiched between the anvil roll 12 and the nip roll 16. At this time, the nip roll 16 and the nip roll support portion 32 are displaced in accordance with the thickness of the part of the layered body 7 sandwiched between the anvil roll 12 and the nip roll 16.

The detection device 40 is provided with a lever 44 and a sensor 48 that detects the displacement of a notch 45 of the lever 44. The lever 44 swings about a support shaft 42, and is pressed against a protruding portion 34 fixed to the nip roll support portion 32. The support shaft 42 is provided on an upper part of a support 41 extending upward from the machine base 11.

Figure 3:
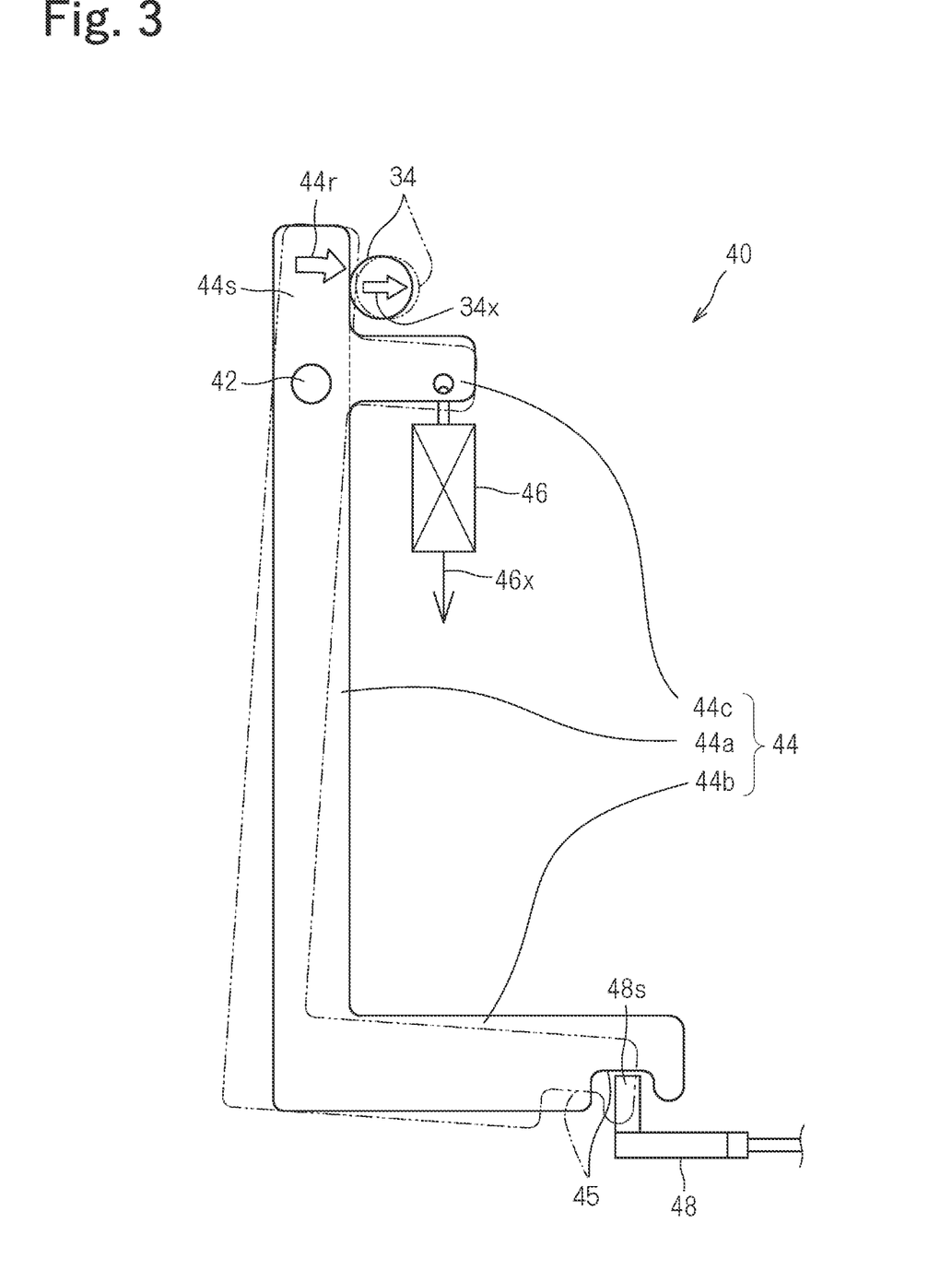
FIG. 3 is a relevant part enlarged view of a detection device (first embodiment).

FIG. 3 is a relevant part enlarged view of the detection device 40. As shown in FIG. 3, the lever 44 has a first piece 44a, a second piece 44b and a third piece 44c. A one end side 44s of the first piece 44a above the support shaft 42 adjoins the protruding portion 34. The second piece 44b is coupled to the other end of the first piece 44a in an L shape, and has the notch 45. The third piece 44c is coupled to the first piece 44a in the vicinity of the support shaft 42 of the first piece 44a so as to extend parallel to the second piece 44b and on the same side as the second piece 44b. The third piece 44c is pulled in a clockwise direction indicated by the arrow 46x by an elastic member 46 such as a spring, and the one end side 44s of the first piece 44a is pressed against the protruding portion 34. When the protruding portion 34 is displaced in the direction indicated by the arrow 34r as shown by the chain line, the lever 44 swings in the direction indicated by the arrow 44r.

The sensor 48 is a photoelectronic sensor, a proximity sensor or the like, and has a detecting portion 48s. The detecting portion 48s is disposed so as to face the notch 45 of the lever 44 shown by the solid line when the thickness of the layered body 7 at the part sandwiched between the anvil roll 12 and the nip roll 16 is within a predetermined reference range and not to face the notch 45 of the lever 44 shown by the solid line when the thickness of the layered body 7 at the part sandwiched between the anvil roll 12 and the nip roll 16 has deviated from the predetermined reference range. Thereby, the sensor 48 detects whether the notch 45 of the lever 44 faces the detecting portion 48s or not.

The detection device 40 detects whether the thickness of the layered body 7 at the part sandwiched between the anvil roll 12 and the nip roll 16 has deviated from the predetermined reference range or not on the basis of the presence or absence of the detection of the notch 45 of the lever 44.

In the lever 44, the distance between the support shaft 42 and the notch 45 is larger than the distance between the support shaft 42 and the protruding portion 34. Thereby, it can be easily detected that the thickness of the layered body 7 has deviated from the predetermined reference range by detecting the displacement of the notch 45 amplified more than the displacement of the protruding portion 34.

As shown in FIG. 1, the signal from the sensor 48 is inputted to the control device 60. The control device 60 is a sequencer or the like that operates according to a predetermined program. The control device 60 controls the air cylinder 26 of the retreat device 20 so that the energy applying device 14 moves to the predetermined position during operation or the retreat position. The control device 60, for example, outputs a control signal to open and close an electromagnetic valve provided on a pipe arrangement or the like that supplies air pressure to the air cylinder 26, thereby extending and contracting the piston rod of the air cylinder 26.

The control device 60 monitors the signal from the sensor 48 of the detection device 40 while the layered sheet manufacturing device 10 is operating, and when it is determined that the thickness of the layered body 7 at the part sandwiched between the anvil roll 12 and the nip roll 16 has deviated from the reference range on the basis of a change of the signal from the sensor 48, controls the retreat device 20 so as to cause the energy applying device 14 to retreat in a direction going away from the anvil roll 12.

When the retreat device 20 causes the energy applying device 14 to retreat in the direction going away from the anvil roll 12 when the detection device 40 detects that the thickness of the layered body 7 at the part sandwiched between the anvil roll 12 and the nip roll 16 has deviated from the reference range as described above, the distance between the anvil roll 12 and the energy applying device 14 is increased before the thickness abnormal part of the layered body 7 where the thickness has deviated from the reference range reaches the space between the anvil roll 12 and the energy applying device 14. And the energy applying device 14 can be made separate from the thickness abnormal part when the thickness abnormal part reaches the space between the anvil roll 12 and the energy applying device 14. This makes it possible to prevent adverse effects, caused by a change in the thickness of the layered body 7, from influencing the energy applying device 14.

For example, when the thickness of the thickness abnormal part of the layered body 7 is larger than the upper limit of the reference range, the thickness abnormal part of the layered body 7 passes through the space between the energy applying device 14 and the anvil roll 12 without colliding with the ultrasonic horn 15 of the energy applying device 14, so that no adverse effects are caused on the energy applying device 14.

When it is detected that the thickness of the layered body 7 at the part sandwiched between the anvil roll 12 and the nip roll 16 is smaller than the lower limit of the reference range during operation, the energy applying device 14 may be caused to retreat in a direction going away from the anvil roll 12.

The feeding roll 56 is driven so as to rotate at a peripheral speed lower than that of the anvil roll 12. By doing this, the layered sheet 8 having stretchability can be manufactured by stretching the elastic stretchable member 6 between the feeding roll 56 and the nip stage 17 and thermally fusing the layers 2, 4 and 6 of the layered body 7 under the condition where the elastic stretchable member 6 is stretched.

As for the first and second stopper rolls 50 and 52 provided in an intermediate position between the nip stage 17 and the feeding roll 56, the size of the space between the first and second stopper rolls 50 and 52 is made a minimum value through which the stretched elastic stretchable member 6 and the first and second continuous sheets 2 and 4 can pass or a value slightly higher than the minimum value.

When the stretched elastic stretchable member 6 breaks downstream of the first and second stopper rolls 50 and 52 to remove the tensile force, the breakage end (the end portion formed by the breakage) upstream of the broken part of the elastic stretchable member 6 returns toward the feeding roll 56 while contracting, and at the same time, the thickness of the breakage end increases. The space between the first and second stopper rolls 50 and 52 is made small to the extent that the thickness-increased part of the breakage end cannot pass through the space between the first and second stopper rolls 50 and 52. This makes the first and second stopper rolls 50 and 52 function as stoppers 50 and 52 that inhibit the breakage end upstream of the broken part of the elastic stretchable member 6 from returning toward the feeding roll 56 beyond the first and second stopper rolls 50 and 52. The breakage end remaining on the downstream side of the first and second stopper rolls 50 and 52 facilitates continuous operation.

Figure 4:
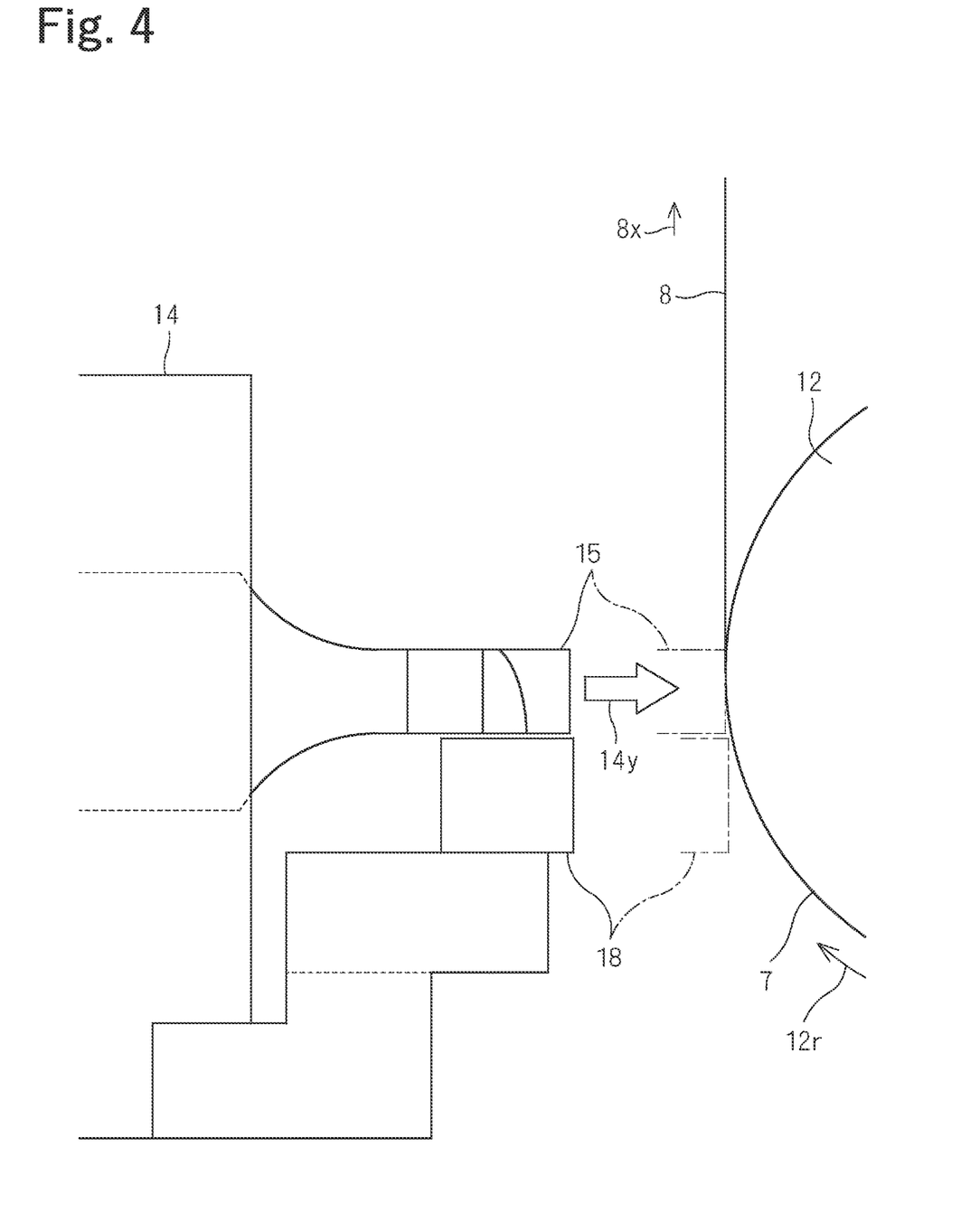
FIG. 4 is a relevant part enlarged view of the layered sheet manufacturing device (first embodiment).

FIG. 4 is a relevant part enlarged view of the layered sheet manufacturing device 10. In FIG. 4, the energy applying device 14 in the retreat position is shown by the solid line. It is preferable to provide a protecting plate 18 as shown in FIG. 4. The protecting plate 18 is fixed to the energy applying device 14 upstream of the ultrasonic horn 15 of the energy applying device 14 with a space from the ultrasonic horn 15. The protecting plate 18 moves integrally with the energy applying device 14.

When the energy applying device 14 is disposed in the predetermined position during operation as shown by the chain line, the protecting plate 18 forms a space from the anvil roll 12 upstream of the space between the ultrasonic horn 15 of the energy applying device 14 and the anvil roll 12. The size of the space between the protecting plate 18 and the anvil roll 12 is made the same as or slightly larger than that of the space between the ultrasonic horn 15 of the energy applying device 14 and the anvil roll 12.

For example, when the elastic stretchable member 6 breaks downstream of the nip stage 17 and it cannot be detected that the thickness of the layered body 7 has deviated from the reference range, or even if it can be detected, when the retreat of the energy applying device 14 is not made in time, if the part increased in thickness by the removal of the tensile force which part is downstream of the broken part of the elastic stretchable member 6 reaches the space between the anvil roll 12 and the energy applying device 14 as it is, the part exerts adverse effects on the energy applying device 14 such as colliding with the ultrasonic horn 15 of the energy applying device 14 to apply a load thereto. When the protecting plate 18 is fixed to the energy applying device 14 in such a case, instead of the ultrasonic horn 15, the protecting plate 18 collides with the thickness-increased part of the layered body 7, which prevents the energy applying device 14 from being influenced by the adverse effects.

Next, a method for manufacturing the layered sheet 8 will be described.

The method for manufacturing the layered sheet 8 is provided with:
(i) a conveyance process in which the layered body 7 containing at least one continuous sheet 2 or 4 is conveyed along a predetermined path;
(ii) a thermal fusion process in which the anvil roll 12 and the energy applying device 14 are disposed so as to sandwich the predetermined path and an energy for thermally fusing the layers 2 and 4 of the layered body 7 together is applied from the energy applying device 14 to the part of the layered body 7 passing through the space between the anvil roll 12 and the energy applying device 14;
(iii) a detection process in which the nip stage 17 is provided where the first and second members 12 and 16 are included that sandwich the layered body 7 in the thickness direction upstream of the space between the anvil roll 12 and the energy applying device 14 and at least one 16 of the first and second members 12 and 16 is the nip roll 16 displaced in accordance with the thickness of the part of the layered body 7 sandwiched between the first and second members, and whether the thickness has deviated from the predetermined reference range or not is determined on the basis of the displacement of the nip roll 16; and
(iv) a retreat process in which when it is determined that the thickness has deviated from the reference range in the detection process, the energy applying device 14 is caused to retreat in the direction going away from the anvil roll 12.

Preferably, the method for manufacturing the layered sheet 8 is further provided with:
(v) a stretching process in which the feeding roll 56 that feeds the elastic stretchable member 6 of which the layered body 7 is to be formed, toward the anvil roll 12 rotates at a peripheral speed lower than that of the anvil roll 12.

More preferably, the method for manufacturing the layered sheet 8 is further provided with:
(vi) a return inhibition process in which the stoppers 50 and 52 are provided in the intermediate position between the nip stage 17 and the feeding roll 56 and when the elastic stretchable member 6 breaks downstream of the intermediate position, the stoppers 50 and 52 inhibit the breakage end upstream of the broken part of the elastic stretchable member 6 from returning toward the feeding roll 56 beyond the intermediate position.

As described above, when the layered sheet 8 is manufactured by using the layered sheet manufacturing device 10, in a case where the layer 4 constituting the layered body 7 breaks or where a foreign substance is mixed in between layers, it is detected that the thickness of the layered body at the part sandwiched between the nip roll 16 and the anvil roll 12 has deviated from the reference range, on the basis of the displacement of the notch 45 of the lever 44 due to the displacement of the nip roll 16, and the energy applying device 14 is caused to retreat in the direction going away from the anvil roll 12, whereby adverse effects caused by a change in the thickness of the layered body 7 such as breakage of the energy applying device 14 can be prevented from influencing the energy applying device 14.

<First modification> In the layered body, it is necessary only that at least one layer be a continuous sheet; the layered body may be formed of either one of the first and second continuous sheets or the layered body may be formed of two or more continuous sheets. The layered body may be formed only of continuous sheets without the supply of the elastic stretchable member 6.

<Second modification> It is not essential that the layered body 7 be conveyed along the outer peripheral surface of the anvil roll 12. For example, the layered body 7 conveyed in a straight line may pass through the space between the anvil roll 12 and the energy applying device 14 to be thermally fused.

<Third modification> The nip stage sandwiching the layered body 7 may be provided upstream of the anvil roll 12 separately from the anvil roll 12. In this case, in the nip stage, it may be one of the first and second members sandwiching the layered body in the thickness direction that serves as the displacement member or it may be both of them that serve as the displacement members. For example, the layered body 7 may be sandwiched in the thickness direction by a nip roll displaced in accordance with the thickness of the layered body 7 which nip roll is formed in the nip stage or upstream of the nip stage and an appropriate member such as a roll or a belt that comes into contact with the layered body 7 without displaced in accordance with the thickness of the layered body 7, or the layered body 7 may be sandwiched in the thickness direction by a pair of nip rolls that are displaced in accordance with the thickness of the layered body 7. The first and second members of the nip stage may be members such as rolls or belts where the parts in contact with the layered body 7 are movable, or may be plate-like members or the like where the parts in contact with the layered body do not move. The first and second members of the nip stage may sandwich the entire part in the width direction of the layered body or may sandwich a part in the width direction of the layered body.

<Fourth modification> In the intermediate position between the nip stage 17 and the feeding roll 56, a stopper may be disposed that has an appropriate structure inhibiting the breakage end upstream of the broken part of the elastic stretchable member 6 from returning toward the feeding roll 56 beyond the intermediate position when the elastic stretchable member 6 breaks downstream of the intermediate position.

For example, using an appropriate member other than a roll, the space through which the elastic stretchable member 6 being stretched between the nip stage 17 and the feeding roll 56 passes is made small to the extent that the breakage end upstream of the broken part of the elastic stretchable member 6 remains downstream of the space when the elastic stretchable member 6 breaks downstream of the space.

Alternatively, an inhibition device may be structured so as to detect a breakage of the elastic stretchable member 6 being stretched between the nip stage 17 and the feeding roll 56 by an image taken by a camera, a tensile force detection mechanism or the like and sandwich the elastic stretchable member 6 to inhibit it from moving when a breakage of the elastic stretchable member 6 is detected.

Figure 5:
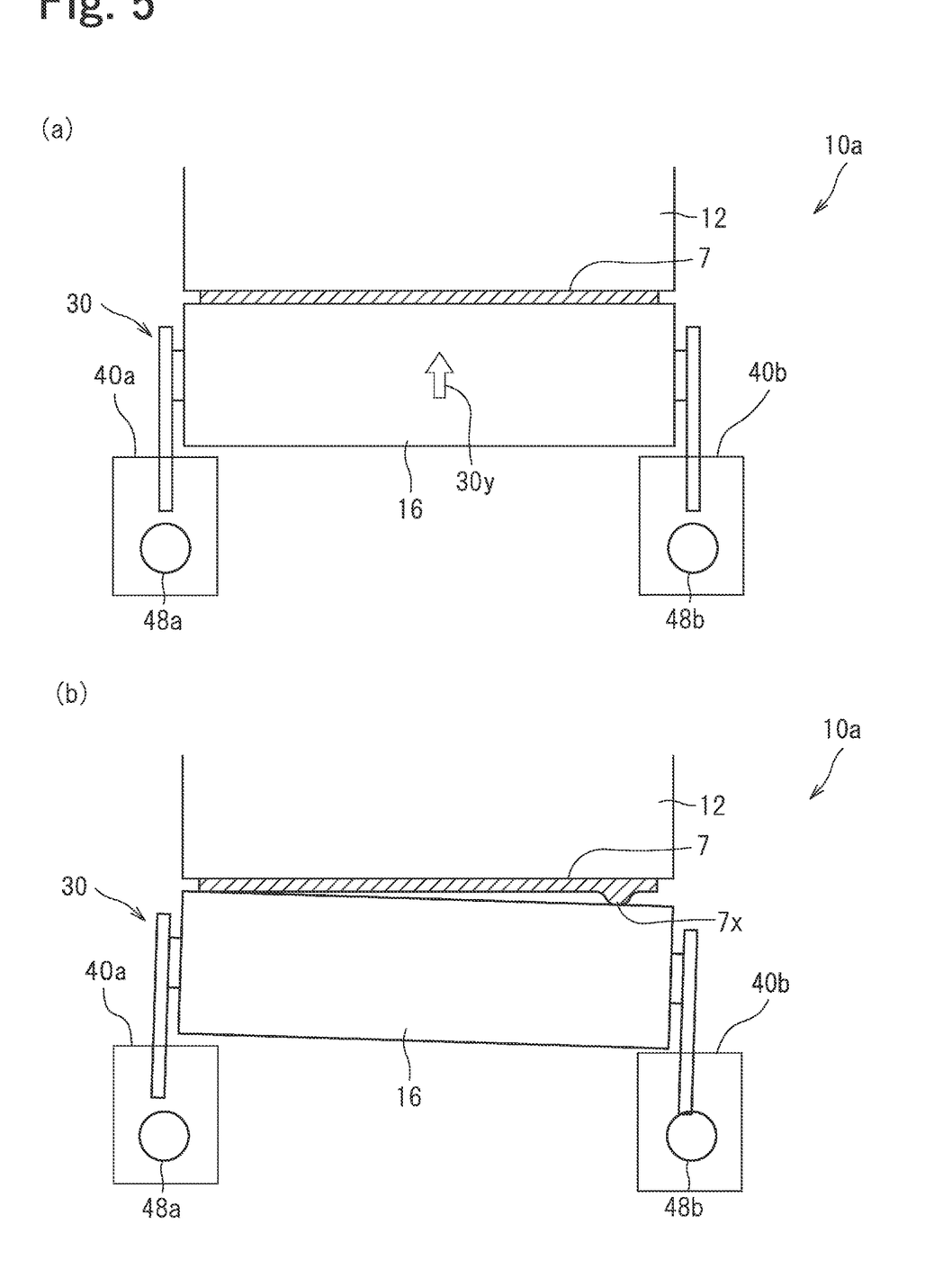
FIGS. 5(a) and 5(b) are schematic views showing a relevant part structure of a layered sheet manufacturing device (second embodiment).

<Second embodiment> FIGS. 5(a) and 5(b) are schematic views conceptually showing a relevant part structure of a layered sheet manufacturing device 10a of a second embodiment. The layered sheet manufacturing device 10a of the second embodiment is provided with two detection devices 40a and 40b. The layered sheet manufacturing device 10a of the second embodiment is structured substantially similarly to the layered sheet manufacturing device 10 of the first embodiment. In the following, structures similar to those of the first embodiment are denoted by the same reference numerals and differences from the first embodiment will be mainly described.

As shown in FIGS. 5(a) and 5(b), the layered sheet manufacturing device 10a of the second embodiment is provided with the first detection device 40a that detects the displacement of one side, in the axial direction, of the nip roll 16 and the second detection device 40b that detects the displacement of the other side, in the axial direction, of the nip roll 16. It is necessary only that the first and second detection devices 40a and 40b be structured properly; for example, they may have the same structure as the detection device 40 of the first embodiment, or may have the same structure as a detection device 40c of a third embodiment described later.

As shown in FIG. 5(a), the nip roll support mechanism 30 that supports the nip roll 16 pushes the nip roll 16 against the anvil roll 12 parallel to the anvil roll 12 as shown by the arrow 30y.

In the nip roll support mechanism 30, backlash sometimes occurs even though the nip roll 16 is structured so as to be displaced in a state of being parallel to the anvil roll 12. For this reason, for example, as shown in FIG. 5(b), when a thickness abnormal part 7x due to a foreign substance or a sheet thickness failure is present on one side, in the width direction, of the layered body 7 and this thickness abnormal part 7x is sandwiched between the anvil roll 12 and the nip roll 16, there are cases where the nip roll 16 is displaced in a state of not being parallel to the anvil roll 12 and the displacement amount on one side, in the axial direction, of the nip roll 16 and the displacement amount on the other side in the axial direction are different. In such cases, even if a sensor 48a of one detection device 40a of the two detection devices 40a and 40b cannot detect the thickness abnormality of the layered body 7, the thickness abnormality of the layered body 7 can be detected by a sensor 48b of the other detection device 40b.

Therefore, by providing the two detection devices 40a and 40b, the thickness abnormality of the layered body 7 can be more reliably detected than when one detection device 40 is provided.

Figure 6:
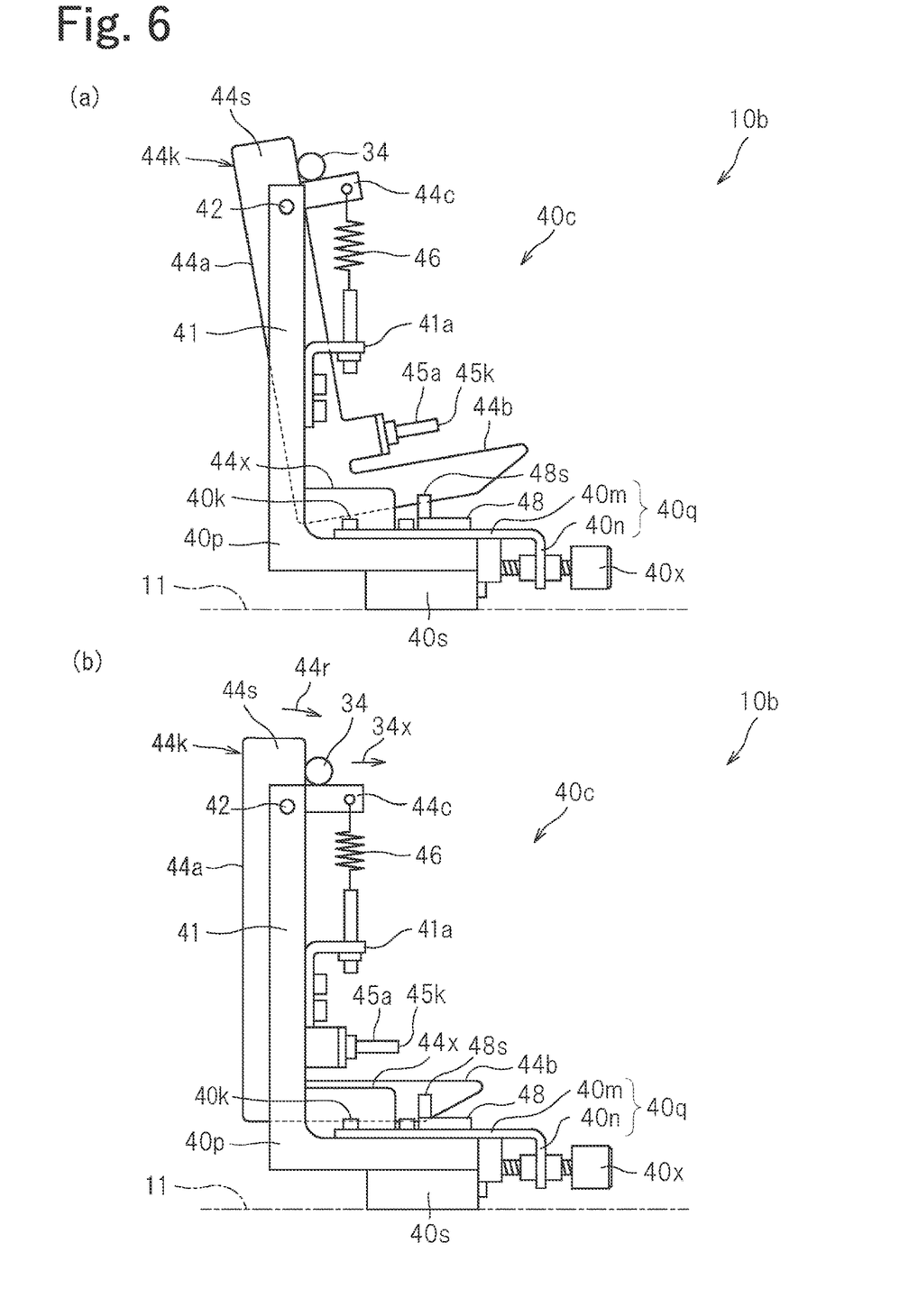
FIGS. 6(a) and 6(b) are schematic views showing a relevant part structure of a layered sheet manufacturing device (third embodiment).

<Third embodiment> FIGS. 6(a) and 6(b) are schematic views showing a relevant part structure of a layered sheet manufacturing device 10b of the third embodiment. The layered sheet manufacturing device 10b of the third embodiment is provided with the detection device 40c that is adjustable in position.

As shown in FIGS. 6(a) and 6(b), the detection device 40c is disposed on a stage 40s. That is, a base portion 40p of the detection device 40c is fixed to an upper portion (movable portion) of the stage 40s, and a lower portion (stationary portion) of the stage 40s is fixed to the machine base 11.

In the detection device 40c, a sensor holding member 40q to which the sensor 48 is fixed is disposed so as to be adjustable in position on the upper surface of the base portion 40p. Specifically, the sensor holding member 40q is disposed so as to be movable along the upper surface of the base portion 40p, and has a sensor fixing portion 40m to which the sensor 48 is fixed and a bent portion 40n bent downward from the sensor fixing portion 40m and disposed along a side surface of the base portion 40p. The sensor fixing portion 40m is fixed to the base portion 40p by a bolt 40k. The bent portion 40n is structured so that the tip of a screw-like position adjustment member 40x engaged with the bent portion 40n abuts on the side surface of the base portion 40p and the position adjustment member 40x is rotated to thereby adjust the position of the sensor fixing portion 40m.

To the base portion 40p, the support 41 is fixed. As in the first embodiment, a lever 44k is supported by the support shaft 42 provided on the support 41. The lever 44k has the first piece 44a, the second piece 44b and the third piece 44c. The third piece 44c of the lever 44k is connected through the elastic member 46 to an attachment portion 41a fixed to the support 41, and one end side 44s of the first piece 44a of the lever 44k is pressed against the protruding portion 34 by the contraction force of the elastic member 46 so that the lever 44k swings in accordance with the displacement of the protruding portion 34. The protruding portion 34 is fixed to the nip roll support portion 32 (see FIGS. 1 and 2) supporting the nip roll 16 as in the first embodiment, or is fixed to a central part of the axial end of the nip roll 16 itself. The lever 44k swings between guide plates 44x disposed on both ends of the lever 44k.

On the lever 44k, unlike the lever 44 of the first embodiment, a bent portion 44d is formed on the first piece 44a, and a protruding member 45a is fixed to the bent portion 44d. The protruding member 45a extends parallel to and in the same direction as the second piece 44b of the lever 44k so that a tip 45k of the protruding member 45a is detected by the sensor 48. The tip 45k of the protruding member 45a is the predetermined part 45k detected by the sensor 48.

For example, when a part of the layered body 7 the thickness of which is within an allowable range is sandwiched between the anvil roll 12 and the nip roll 16, the first piece 44a of the lever 44k is inclined as shown in FIG. 6(a), so that the tip 45k of the protruding member 45a is situated above the detecting portion 48s of the sensor 48 to be detected.

When the thickness abnormal part of the layered body 7 is sandwiched between the anvil roll 12 and the nip roll 16, as shown in FIG. 6(b), the protruding portion 34 moves in the direction indicated by the arrow 34x, so that the lever 44k swings in the direction indicated by the arrow 44r. Consequently, the tip 45k of the protruding member 45a moves away from above the detecting portion 48s of the sensor 48, so that the tip 45k of the protruding member 45a is not detected.

In the layered sheet manufacturing device 10b of the third embodiment, the detection by the sensor 48 can be easily adjusted so as to be adapted to the reference value or the allowable range of the thickness of the layered body 7.

For example, when the reference value of the thickness of the layered body 7 is changed by a switching of the kind of the layered sheet 8 or the like, the position of the protruding portion 34 when the part of the layered body 7 the thickness of which is the reference value is sandwiched between the anvil roll 12 and the nip roll 16, that is, the reference position is changed. In this case, by using the stage 40s, for example, the position of the layered sheet manufacturing device 10b is adjusted so that the position of the layered sheet manufacturing device 10b relative to the reference position of the protruding portion 34 is the same.

In a case where the allowable range of the thickness of the layered body 7 is changed, when the thickness of the layered sheet 8 sandwiched between the anvil roll 12 and the nip roll 16 is within the allowable range, that is, when the angle of the lever 44k is within a predetermined range, the sensor 48 detects the tip 45k of the protruding member 45a, whereas when the thickness of the layered sheet 8 has deviated from the allowable range and the angle of the lever 44k has deviated from the predetermined range, the position of the sensor holding member 40q is adjusted so that the sensor 48 does not detect the tip 45k of the protruding member 45a.

Instead of the position adjustment of the sensor 48 by the sensor holding member 40q or in addition to the position adjustment of the sensor 48, the position of the tip 45k of the protruding member 45a that the sensor 48 detects may be made adjustable. For example, a structure may be adopted in which the position of the tip 45k of the protruding member 45a is adjustable by adjusting the length along which the protruding member 45a is attached to the bent portion 44d.

<Summary> As described above, with the layered sheet manufacturing devices 10, 10a and 10b and the method for manufacturing the layered sheet 8, it is possible to prevent adverse effects, caused by a change in the thickness of the layered sheet 8, from influencing the energy applying device 14. Consequently, continuous operation is facilitated.

The present invention is not limited to the above-described embodiments but may be carried out with various modifications being added.

For example, a layered sheet containing a plurality of elastic stretchable members may be manufactured. A layered body may be manufactured in which on a continuous sheet, another layer is laminated with an interval in the conveyance direction of the continuous sheet.

DESCRIPTION OF REFERENCE NUMERALS 2, 4 Continuous sheet
6 Elastic stretchable member
7 Layered body
8 Layered sheet
10, 10a, 10b Layered sheet manufacturing device
12 Anvil roll (first member)
14 Energy applying device
16 Nip roll (second member, displacement member)
17 Nip stage
20 Retreat device
40, 40a, 40b, 40c Detection device
44, 44k Lever
45 Notch (predetermined part)
45k Tip (predetermined part)
48, 48a, 48b Sensor
50, 52 Stopper roll (stopper)
56 Feeding roll

The invention claimed is:

1. A layered sheet manufacturing device comprising:
an anvil roll that faces a predetermined path along which a layered body containing at least one continuous sheet, and another sheet or layer is conveyed;
an energy applying device disposed so as to face the anvil roll across the predetermined path and applying an energy for thermally fusing layers of the layered body together, to the layered body being conveyed along the predetermined path;
a nip stage including first and second members sandwiching the layered body upstream of a space between the anvil roll and the energy applying device, at least one of the first and second members being a displacement member displaced according to a thickness of a part of the layered body sandwiched between the first and second members;
a detection device that detects whether the thickness has deviated from a predetermined reference range or not on a basis of a displacement of the displacement member; and
a retreat device that causes the energy applying device to retreat in a direction going away from the anvil roll when the detection device detects that the thickness has deviated from the reference range,
wherein the detection device includes:
a lever that swings according to the displacement of the displacement member and having a predetermined part displaced more largely than the displacement member; and
a sensor that detects a displacement of the predetermined part of the lever.

2. The layered sheet manufacturing device according to claim 1, wherein the energy applying device comes into contact with the layered body to apply a vibrational energy or a thermal energy to the layered body.

3. The layered sheet manufacturing device according to claim 1, wherein the nip stage is structured so as to sandwich the layered body in a direction of the thickness between the anvil roll and the displacement member.

4. The layered sheet manufacturing device according to claim 1, further comprising a feeding roll that feeds an elastic stretchable member of which the layered body is to be formed, toward the anvil roll,
wherein the feeding roll rotates at a peripheral speed lower than a peripheral speed of the anvil roll.

5. The layered sheet manufacturing device according to claim 4, further comprising a stopper disposed in an intermediate position between the nip stage and the feeding roll and when the elastic stretchable member breaks downstream of the intermediate position, inhibiting a breakage end upstream of a broken part of the elastic stretchable member from returning toward the feeding roll beyond the intermediate position.

6. A layered sheet manufacturing method comprising:
a conveyance process in which a layered body containing at least one continuous sheet, and another sheet or layer is conveyed along a predetermined path;
a thermal fusion process in which an anvil roll and an energy applying device are disposed so as to sandwich the predetermined path and an energy for thermally fusing layers of the layered body together is applied from the energy applying device to a part of the layered body passing through a space between the anvil roll and the energy applying device;
a detection process in which a nip stage is provided where first and second members are included, the first and second members sandwiching the layered body in a thickness direction upstream of the space between the anvil roll and the energy applying device and at least one of the first and second members is a displacement member displaced in accordance with a thickness of the part of the layered body sandwiched between the first and second members, and whether the thickness has deviated from a predetermined reference range or not is determined on the basis of a displacement of the displacement member; and
a retreat process in which when it is determined that the thickness has deviated from the reference range in the detection process, the energy applying device is caused to retreat in the direction going away from the anvil roll, wherein in the detection process, by using a lever that swings according to the displacement of the displacement member and having a predetermined part displaced more largely than the displacement member and a sensor that detects a displacement of the predetermined part of the lever, it is detected whether the thickness has deviated from the reference range or not.

7. The layered sheet manufacturing method according to claim 6, wherein the energy applying device comes into contact with the layered body to apply a vibrational energy or a thermal energy to the layered body.

8. The layered sheet manufacturing method according to claim 6, wherein the nip stage is structured so as to sandwich the layered body in a direction of the thickness between the anvil roll and the displacement member.

9. The layered sheet manufacturing method according to claim 6, wherein a stretching process is further provided in which a feeding roll that feeds an elastic stretchable member which forms the layered body toward the anvil roll rotates at a peripheral speed lower than a peripheral speed of the anvil roll.

10. The layered sheet manufacturing method according to claim 9, wherein a return inhibition process is further provided in which a stopper is provided in an intermediate position between the nip stage and the feeding roll and when the elastic stretchable member breaks downstream of the intermediate position, the stopper inhibits a breakage end upstream of a broken part of the elastic stretchable member from returning toward the feeding roll beyond the intermediate position.

11. The layered sheet manufacturing device according to claim 1, wherein the first member of the nip stage is the anvil roll, and the second member of the nip stage is a nip roll contacting the anvil roll through the layered body, the nip roll being arranged to be movable relative to the anvil roll to form the nip stage.

12. The layered sheet manufacturing method according to claim 6, wherein the first member of the nip stage is the anvil roll, and the second member of the nip stage is a nip roll contacting the anvil roll through the layered body, the nip roll being arranged to be movable relative to the anvil roll to form the nip stage.

\* \* \* \* \*